US011795121B2

(12) United States Patent
Kamata et al.

(10) Patent No.: US 11,795,121 B2
(45) Date of Patent: Oct. 24, 2023

(54) HYDROCARBON GENERATION SYSTEM AND HYDROCARBON GENERATION METHOD

(71) Applicant: IHI CORPORATION, Tokyo (JP)

(72) Inventors: Hiroyuki Kamata, Tokyo (JP); Wonyoung Choi, Tokyo (JP); Toshiyuki Suda, Tokyo (JP); Kentaro Nariai, Tokyo (JP)

(73) Assignee: IHI CORPORATION, Tokyo (JP)

( * ) Notice: Subject to any disclaimer, the term of this patent is extended or adjusted under 35 U.S.C. 154(b) by 0 days.

(21) Appl. No.: 17/857,255

(22) Filed: Jul. 5, 2022

(65) Prior Publication Data

US 2022/0332663 A1 Oct. 20, 2022

Related U.S. Application Data

(63) Continuation of application No. PCT/JP2021/011401, filed on Mar. 19, 2021.

(30) Foreign Application Priority Data

Mar. 23, 2020 (JP) .................. 2020-051245

(51) Int. Cl.
*C07C 1/12* (2006.01)
*C07C 1/10* (2006.01)
(Continued)

(52) U.S. Cl.
CPC ................ *C07C 1/12* (2013.01); *C07C 1/042* (2013.01); *C07C 1/044* (2013.01); *C07C 1/0485* (2013.01);
(Continued)

(58) Field of Classification Search
CPC ....... C07C 1/042; C07C 1/044; C07C 1/0485; C07C 1/11; C07C 1/12; C07C 2523/745;
(Continued)

(56) References Cited

U.S. PATENT DOCUMENTS 4,794,099 A 12/1988 Iglesia et al.
9,789,437 B2 * 10/2017 Tanaka ............... B01D 53/1475
(Continued)

FOREIGN PATENT DOCUMENTS

JP H02-073023 A 3/1990
JP 2007-503503 A 2/2007
(Continued)

OTHER PUBLICATIONS

Hiroyuki Kamata, "Catalyst for CO2 Conversion to Fuel and Useful Chemicals," Journal of IHI Technologies, vol. 59, No. 1, 2019, pp. 16-20.
(Continued)

*Primary Examiner* — In Suk C Bullock
*Assistant Examiner* — Jason Y Chong

(57) ABSTRACT

A hydrocarbon generation system includes a first generation apparatus configured to generate a hydrocarbon with two or more carbon atoms from a first raw material containing: at least one of carbon monoxide or carbon dioxide; and hydrogen. The hydrocarbon generation system includes a second generation apparatus configured to generate methane from a second raw material including: hydrogen; and at least one of carbon monoxide or carbon dioxide contained in the first raw material and discharged from the first generation apparatus.

10 Claims, 1 Drawing Sheet

(51) Int. Cl.
   *C07C 1/04*    (2006.01)
   *C07C 7/11*    (2006.01)
(52) U.S. Cl.
   CPC .......... *C07C 7/11* (2013.01); *C07C 2523/745* (2013.01); *C07C 2523/755* (2013.01)
(58) Field of Classification Search
   CPC ... C07C 2523/755; Y02A 50/20; Y02P 20/50; Y02P 20/52; B01D 53/62
   See application file for complete search history.

(56) References Cited

U.S. PATENT DOCUMENTS

| | | |
|---|---|---|
| 2007/0142481 A1 | 6/2007 | Steynberg et al. |
| 2012/0329890 A1 | 12/2012 | Ono et al. |
| 2013/0041051 A1 | 2/2013 | Zuberbuhler et al. |
| 2013/0317264 A1 | 11/2013 | Barradas et al. |
| 2014/0303266 A1 | 10/2014 | Hyman |
| 2015/0139878 A1 | 5/2015 | Tanaka et al. |
| 2015/0328622 A1 | 11/2015 | Ono et al. |
| 2016/0115034 A1 | 4/2016 | Watanabe et al. |
| 2016/0153316 A1 | 6/2016 | Bergins et al. |
| 2016/0237858 A1 | 8/2016 | Bergins et al. |
| 2021/0275994 A1 | 9/2021 | Takano et al. |

FOREIGN PATENT DOCUMENTS

| | | |
|---|---|---|
| JP | 2009-077457 A | 4/2009 |
| JP | 2013-515684 A | 5/2013 |
| JP | 2014-036942 A | 2/2014 |
| JP | 2014-514130 A | 6/2014 |
| JP | 2014-534902 A | 12/2014 |
| JP | 2016-132644 A | 7/2016 |
| JP | 2016-531973 A | 10/2016 |
| JP | 2018-020278 A | 2/2018 |
| JP | 2019-142808 A | 8/2019 |
| JP | 2020-037535 A | 3/2020 |
| JP | 2020-083799 A | 6/2020 |
| WO | 2011/108347 A1 | 9/2011 |
| WO | 2014/192381 A1 | 12/2014 |

OTHER PUBLICATIONS

Tao Ren et al., "Olefins from conventional and heavy feedstocks: Energy use in steam cracking and alternative processes," Energy, vol. 31, 2006, pp. 425-451.

Thomas Riedel et al., "Comparative study of Fischer-Tropsch synthesis with H2/CO and H2/CO2 syngas using Fe- and Co-based catalysts," Applied Catalysis A: General, vol. 186, 1999, pp. 201-213.

Japan Patent Office, "Notice of Reasons for Refusal", issued in Japanese Patent Application No. 2022-510426, which is a counterpart to U.S. Appl. No. 17/857,255, dated May 23, 2023, 7 pages.

* cited by examiner

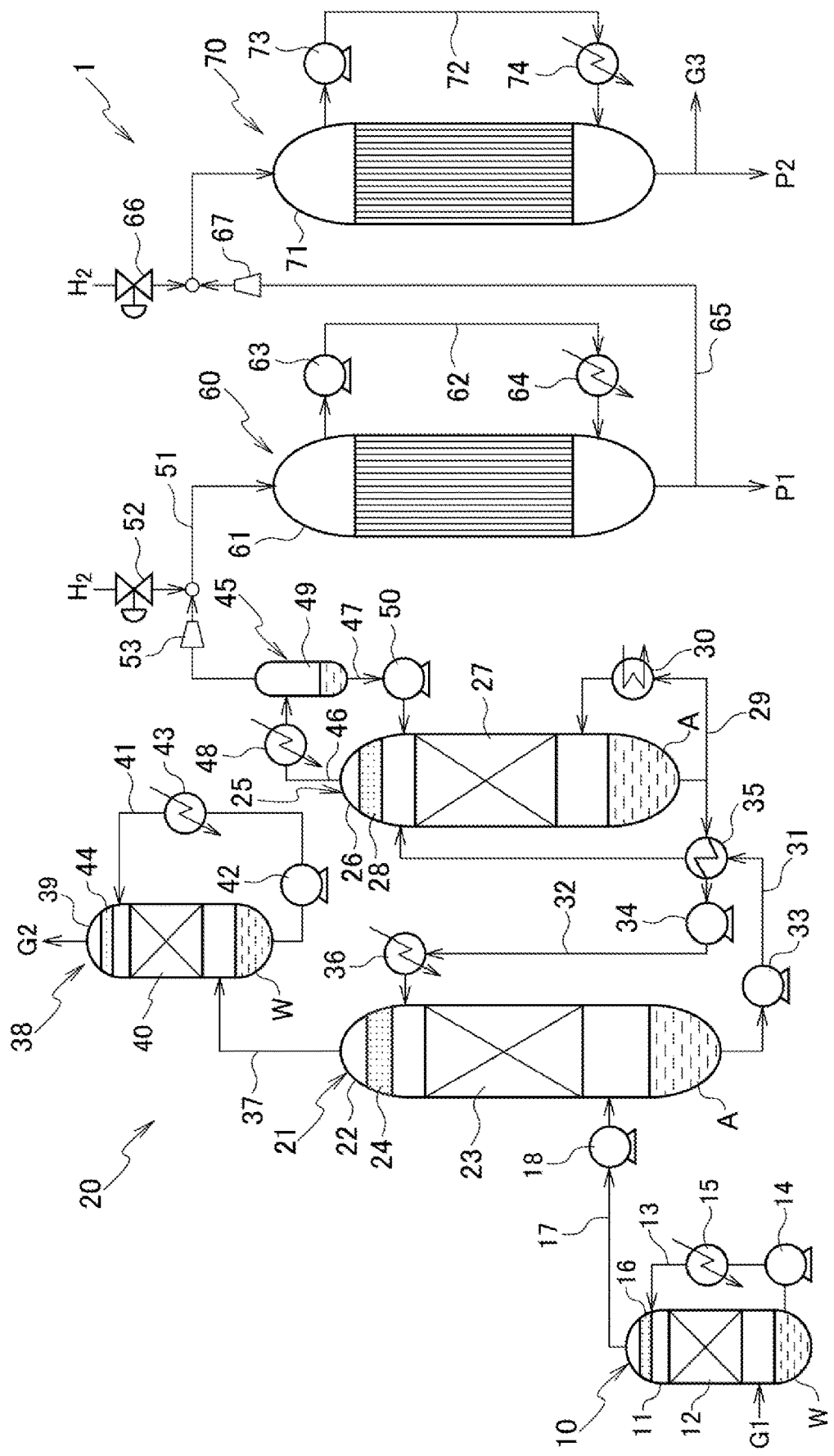

HYDROCARBON GENERATION SYSTEM AND HYDROCARBON GENERATION METHOD

CROSS REFERENCE TO RELATED APPLICATIONS

This application is a continuation application of International Application No. PCT/JP2021/011401, filed on Mar. 19, 2021, which claims priority to Japanese Patent Application No. 2020-051245, filed on Mar. 23, 2020, the entire contents of which are incorporated by reference herein.

BACKGROUND

1. Technical Field

The present disclosure relates to a hydrocarbon generation system and a hydrocarbon generation method.

2. Description of the Related Art

Methane is a main component of natural gas and city gas and is used as a fuel in existing combustion and power generation facilities. Methane is generated, for example, from a raw material gas containing hydrogen and carbon dioxide. Patent Literature 1 discloses a method of generating methane from a raw material gas containing hydrogen and carbon dioxide using at least two reactors.

CITATION LIST

Patent Literature 1: Japanese Translation of PCT International Application Publication No. 2013-515684

SUMMARY

Carbon dioxide has been regarded as a cause of global warming, and there has been a worldwide movement to curb carbon dioxide emissions. Utilization of carbon dioxide contained in plant exhaust gases and the like can reduce carbon dioxide emissions and generate methane, a valuable resource. Methane can be generated from a raw material containing carbon monoxide as well as from a raw material containing carbon dioxide. Carbon monoxide is found in plant exhaust gases and in combustion gases of hydrocarbons in biomass and waste.

Meanwhile, hydrocarbons, such as ethylene and propylene, which are raw materials for plastics or resins, are traded at a higher price than methane and can be generated from raw materials containing carbon monoxide or carbon dioxide. The production of plastics or resins from carbon dioxide can reduce the emission of carbon dioxide into the atmosphere and provide carbon-neutral plastics or resins. However, the rate at which such hydrocarbons are generated from raw materials containing carbon monoxide or carbon dioxide is lower than the rate at which methane is generated, and a large amount of unreacted carbon monoxide or carbon dioxide is discharged.

An object of the present disclosure is to provide a hydrocarbon generation system, a first generation apparatus, a second generation apparatus, and a hydrocarbon generation method capable of efficiently generating methane and a hydrocarbon other than methane from at least one of carbon monoxide or carbon dioxide.

A hydrocarbon generation system according to an aspect of the present disclosure includes a first generation apparatus that generates a hydrocarbon with two or more carbon atoms from a first raw material including: at least one of carbon monoxide or carbon dioxide; and hydrogen. The hydrocarbon generation system includes a second generation apparatus that generates methane from a second raw material including: hydrogen; and at least one of carbon monoxide or carbon dioxide contained in the first raw material and discharged from the first generation apparatus.

The first generation apparatus may generate the hydrocarbon with two or more carbon atoms from 20% by mass or more and less than 85% by mass of the carbon dioxide contained in the first raw material. The second generation apparatus may generate the methane from 85% by mass or more of the carbon dioxide contained in the second raw material. The first generation apparatus may be provided with an iron catalyst for generating the hydrocarbon with two or more carbon atoms from the first raw material, and the second generation apparatus may be provided with a nickel catalyst for generating the methane from the second raw material. The hydrocarbon generation system may further include a carbon dioxide capture apparatus that captures carbon dioxide from a gas containing carbon dioxide, and the carbon dioxide contained in the first raw material may include carbon dioxide separated at the carbon dioxide capture apparatus. The carbon dioxide capture apparatus may include an absorption apparatus that forms an alkaline solution containing carbon dioxide by gas-liquid contact between a gas containing carbon dioxide and an alkaline solution; and a separation apparatus that separates carbon dioxide from the alkaline solution containing carbon dioxide, and the carbon dioxide contained in the first raw material may include the carbon dioxide separated at the separation apparatus. At least a part of one of heat of reaction when the hydrocarbon with two or more carbon atoms is generated in the first generation apparatus, or heat of reaction when the methane is generated in the second generation apparatus may be recovered. The separation apparatus may separate carbon dioxide from the alkaline solution containing carbon dioxide by using at least a part of one of heat of reaction when the hydrocarbon with two or more carbon atoms is generated in the first generation apparatus; or heat of reaction when the methane is generated in the second generation apparatus. The hydrocarbon with two or more carbon atoms may include an olefin with two or more and four or less carbon atoms. A gas discharged from the first generation apparatus may be supplied to the second generation apparatus with the pressure of the gas being maintained.

A first generation apparatus according to another aspect of the present disclosure generates a hydrocarbon with two or more carbon atoms from a first raw material containing: at least one of carbon monoxide or carbon dioxide; and hydrogen, and is connected to a second generation apparatus. The second generation apparatus generates methane from a second raw material containing: hydrogen; and at least one of carbon monoxide or carbon dioxide contained in the first raw material and discharged from the first generation apparatus.

A second generation apparatus according to another aspect of the present disclosure generates methane from a second raw material containing: hydrogen; and at least one of carbon monoxide or carbon dioxide contained in a first raw material and discharged from a first generation apparatus. The first generation apparatus generates a hydrocarbon with two or more carbon atoms from the first raw material containing: at least one of carbon monoxide or carbon dioxide; and hydrogen.

A hydrocarbon generation method according to another aspect of the present disclosure includes a first generation step of generating a hydrocarbon with two or more carbon atoms from a first raw material including: at least one of carbon monoxide or carbon dioxide; and hydrogen. The hydrocarbon generation method includes a second generation step of generating methane from a second raw material including: hydrogen; and at least one of carbon monoxide or carbon dioxide contained in the first raw material and discharged in the first generation step.

The present disclosure provides a hydrocarbon generation system, a first generation apparatus, a second generation apparatus, and a hydrocarbon generation method capable of efficiently generating methane and a hydrocarbon other than methane from at least one of carbon monoxide or carbon dioxide.

BRIEF DESCRIPTION OF THE DRAWINGS

The FIGURE is a schematic diagram illustrating a hydrocarbon generation system according to some embodiments.

DESCRIPTION OF THE EMBODIMENTS

Some exemplary embodiments are described below with reference to the drawings. Note that dimensional ratios in the drawings are exaggerated for convenience of explanation and may differ from the actual ratios.

[Hydrocarbon Generation System]

As illustrated in the FIGURE, a hydrocarbon generation system 1 includes a pretreatment apparatus 10, a carbon dioxide capture apparatus 20, a first generation apparatus 60, and a second generation apparatus 70.

The pretreatment apparatus 10 cools a gas G1 containing carbon dioxide. The gas G1 is an exhaust gas, such as a combustion exhaust gas generated by combustion of a fuel in a thermal power plant, an iron mill, or the like, or a process exhaust gas from a chemical plant or the like. The gas G1 may also be a gas containing carbon dioxide in an oil refining or petrochemical process. As described below, carbon dioxide is absorbed into an alkaline solution A at an absorption apparatus 21 of the carbon dioxide capture apparatus 20. When the temperature of the alkaline solution A is low, the absorption rate of carbon dioxide to the alkaline solution A is high, which improves the efficiency of carbon dioxide capture by the carbon dioxide capture apparatus 20. Thus, cooling the gas G1 containing carbon dioxide by means of the pretreatment apparatus 10 prevents the temperature in the absorption apparatus 21 from rising due to the gas G1. However, the pretreatment apparatus 10 is not always necessary, such as when the gas G1 does not have a high temperature, or when there is no great influence on the efficiency of carbon dioxide capture by the carbon dioxide capture apparatus 20. The pretreatment apparatus 10 is, for example, a countercurrent gas-liquid contact apparatus and includes a cooling tank 11, a filling material 12, a cooling pipe 13, a pump 14, a cooler 15, a demister 16, an air pipe 17, and a pump 18.

The cooling tank 11 is provided with the filling material 12 therein. The filling material 12 is provided to increase a contact area between the gas G1 supplied to the pretreatment apparatus 10 and cooling water W and brings the supplied gas G1 into gas-liquid contact with the cooling water W. The filling material 12 is made from an iron-based metal material, such as stainless steel or carbon steel; however, it is not limited to this material, and a material having durability and corrosion resistance at the processing temperature and having a shape with a desired contact area can be appropriately selected and used.

The cooling pipe 13, the pump 14, and the cooler 15 are arranged outside the cooling tank 11. The cooling pipe 13 connects an upper part of the cooling tank 11, which is above the filling material 12, and a bottom part of the cooling tank 11, which is below the filling material 12. The cooling pipe 13 is provided with the pump 14 and the cooler 15. The cooling water W remaining at the bottom part of the cooling tank 11 is sucked up by the pump 14 from the bottom part of the cooling tank 11, cooled by the cooler 15, and then sent to the upper part of the cooling tank 11.

The gas G1 is supplied from a gas supply port provided below the filling material 12 in the cooling tank 11. The gas G1 supplied from the gas supply port rises in the cooling tank 11, and gas-liquid contact with the cooling water W supplied from the upper part of the cooling tank 11 is promoted in the filling material 12 to cool the gas G1 to an appropriate temperature. The cooled gas G1 passes through the demister 16, which removes minute droplets, and is discharged from a gas discharge port provided at the top of the cooling tank 11. The gas discharge port of the pretreatment apparatus 10 and a bottom part of an absorption tank 22 of the carbon dioxide capture apparatus 20 are connected by the air pipe 17, which is provided with the pump 18. The gas G1 discharged from the gas discharge port of the pretreatment apparatus 10 is supplied to the absorption apparatus 21 through the air pipe 17 by the pump 18.

Meanwhile, the cooling water W, the temperature of which has risen by contact with the gas G1 at the filling material 12, flows down to the bottom part of the cooling tank 11, passes through the cooling pipe 13 and is cooled by the cooler 15 again, and is then supplied from the upper part of the cooling tank 11.

When the gas G1 includes a catalyst poison, the pretreatment apparatus 10 may be configured to remove the catalyst poison from the gas G1. The pretreatment apparatus 10 is usable to remove impurities contained in the gas G1 and poisoning the alkaline solution A and catalysts used in the first generation apparatus 60 and the second generation apparatus 70, for example. Examples of the impurities include sulfur compounds, such as a sulfur dioxide, hydrogen sulfide, and a carbonyl sulfide. In this case, the cooling tank 11 is also referred to as an absorption tank.

The carbon dioxide capture apparatus 20 captures carbon dioxide from the gas G1 containing carbon dioxide. Specifically, the carbon dioxide capture apparatus 20 generates, from the gas G1 containing carbon dioxide to be captured, a gas having a carbon dioxide concentration higher than that of the capture-target gas G1. The carbon dioxide capture apparatus 20 is able to capture carbon dioxide by a chemical absorption method, a pressure swing adsorption method, a temperature swing adsorption method, or a membrane separation and concentration method, for example. The present embodiment describes the carbon dioxide capture apparatus 20 using the chemical absorption method as an example. The chemical absorption method captures a large amount of carbon dioxide from a gas at atmospheric pressure. The carbon dioxide capture apparatus 20 includes the absorption apparatus 21, a separation apparatus 25, a supply pipe 31, a reflux pipe 32, a pump 33, a pump 34, a heat exchanger 35, a cooler 36, an air pipe 37, a cleaning apparatus 38, and a gas-liquid separation unit 45.

The absorption apparatus 21 forms an alkaline solution A containing carbon dioxide by gas-liquid contact between a gas containing carbon dioxide and the alkaline solution A.

The separation apparatus 25 separates carbon dioxide from the alkaline solution A containing carbon dioxide. The alkaline solution A may contain, for example, at least one absorbent of an alkanolamine or a hindered amine having an alcoholic hydroxyl group. The alkanolamine may be, for example, at least one amine selected from the group consisting of a monoethanolamine, a diethanolamine, a triethanolamine, a methyldiethanolamine, a diisopropanolamine, and a diglycolamine. The hindered amine having an alcoholic hydroxyl group may be, for example, at least one amine selected from the group consisting of 2-amino-2-methyl-1-propanol (AMP), 2-(ethylamino) ethanol (EAE), and 2-(methylamino) ethanol (MAE). Preferably, the alkaline solution A contains a monoethanolamine (MEA). The concentration of the absorbent in the alkaline solution A can be set appropriately according to the amount of carbon dioxide contained in the gas to be treated, treatment speed, or the like, and is, for example, 10 to 50% by mass in consideration of fluidity, reduction of consumption loss, and the like of the alkaline solution A.

The absorption apparatus 21, the separation apparatus 25, and the cleaning apparatus 38 are countercurrent gas-liquid contact apparatuses, for example. The absorption apparatus 21 includes the absorption tank 22, a filling material 23, and a demister 24. The separation apparatus 25 includes a separation tank 26, a filling material 27, a demister 28, a circulation pipe 29, and a heater 30.

The supply pipe 31 connects the bottom part of the absorption tank 22, which is below the filling material 23 in the absorption apparatus 21, and an upper part of the separation tank 26, which is above the filling material 27 in the separation apparatus 25. The reflux pipe 32 connects a bottom part of the separation tank 26, which is below the filling material 27 in the separation apparatus 25, and an upper part of the absorption tank 22, which is above the filling material 23 in the absorption apparatus 21. The supply pipe 31 is provided with the pump 33, and the reflux pipe 32 is provided with the pump 34 and the cooler 36. The supply pipe 31 and the reflux pipe 32 are provided with the heat exchanger 35.

The type of heat exchanger 35 is not limited, and, for example, a spiral type, a plate type, a double tube type, a multiple cylinder type, a multiple circular-tube type, a spiral tube type, a spiral plate type, a tank coil type, a tank jacket type, and a direct contact liquid type are usable.

The gas G1 supplied to below the filling material 23 in the absorption apparatus 21 rises in the absorption tank 22 while coming into gas-liquid contact with an alkaline solution A supplied from the upper part of the absorption tank 22, and carbon dioxide contained in the gas G1 is absorbed into the alkaline solution A. While rising in the absorption tank 22, the gas G1 passes through the filling material 23, and thus the gas-liquid contact with the alkaline solution A is promoted. The alkaline solution A having absorbed carbon dioxide drips down from the filling material 23 to a bottom part of the absorption tank 22 and remains at the bottom part of the absorption tank 22. The alkaline solution A remaining at the bottom part of the absorption tank 22 is sucked up by the pump 33, passes through the supply pipe 31, is heated by the heat exchanger 35, and is then sent to above the filling material 27 in the separation apparatus 25.

The alkaline solution A heated by the heat exchanger 35 drips down from above the filling material 27 while releasing carbon dioxide, and remains at the bottom part of the separation tank 26. At this time, the alkaline solution A passes through the filling material 27, and the release of carbon dioxide from the alkaline solution A is promoted by gas-liquid contact at the filling material 27. The circulation pipe 29 is provided at the bottom part of the separation tank 26 and provided with the heater 30, which is a steam type. A part of the alkaline solution A remaining at the bottom part of the separation tank 26 is diverted to the heater 30 through the circulation pipe 29, heated to, for example, the vicinity of the boiling point of the alkaline solution A by heat exchange with high temperature steam, and then refluxed into the separation tank 26. The heating makes carbon dioxide be released from the alkaline solution A at the bottom part of the separation tank 26. The heating also indirectly heats the filling material 27, and the release of carbon dioxide from the alkaline solution A is promoted by the gas-liquid contact at the filling material 27. A gas containing discharged carbon dioxide passes through the demister 28, which removes minute droplets, and is discharged from a gas discharge port provided at the top of the separation tank 26.

Meanwhile, a part of the alkaline solution A remaining at a bottom part of the separation tank 26 is sucked up by the pump 34, passes through the reflux pipe 32, is cooled by the heat exchanger 35, and is then sent to above the filling material 23 in the absorption apparatus 21. At this time, the alkaline solution A passing through the supply pipe 31 and the alkaline solution A passing through the reflux pipe 32 perform heat exchange, and thus the alkaline solution A passing through the supply pipe 31 is heated, and the alkaline solution A passing through the reflux pipe 32 is cooled. The alkaline solution A passing through the reflux pipe 32 is further cooled by the cooler 36 provided downstream of the heat exchanger 35. The alkaline solution A supplied from above the filling material 23 of the absorption apparatus 21 comes into gas-liquid contact with the gas G1 supplied from the pretreatment apparatus 10, and carbon dioxide is absorbed into the alkaline solution A again.

A gas from which carbon dioxide has been removed in the absorption tank 22 passes through the demister 24, which removes minute droplets, and is discharged from a gas discharge port provided at the top of the absorption tank 22. The gas discharge port of the absorption tank 22 and a bottom part of a cleaning tank 39 of the cleaning apparatus 38 are connected by the air pipe 37, and the gas discharged from the absorption apparatus 21 is supplied to the cleaning apparatus 38 through the air pipe 37.

The cleaning apparatus 38 removes the alkaline solution A from the gas discharged from the top of the absorption tank 22. The cleaning apparatus 38 includes the cleaning tank 39, a filling material 40, a cooling pipe 41, a pump 42, a cooler 43, and a demister 44. The filling material 40 is arranged inside the cleaning tank 39. The cooling pipe 41, the pump 42, and the cooler 43 are arranged outside the cleaning tank 39. The cooling pipe 41 connects an upper part of the cleaning tank 39, which is above the filling material 40, and a bottom part of the cleaning tank 39, which is below the filling material 40. The cooling pipe 41 is provided with the pump 42 and the cooler 43. Cooling water W remaining at the bottom part of the cleaning tank 39 is sucked up from the bottom part of the cleaning tank 39 by the pump 42, cooled by the cooler 43, and then sent to the upper part of the cleaning tank 39.

The gas sent from the absorption apparatus 21 is supplied from a gas supply port provided below the filling material 40 in the cleaning tank 39. The gas supplied from the gas supply port rises in the cleaning tank 39, gas-liquid contact with the cooling water W supplied from the upper part of the cleaning tank 39 is promoted in the filling material 40, and the alkaline solution A contained in the gas is removed. The gas from which the alkaline solution A is removed passes through the demister 44, which removes minute droplets, and is discharged as a gas G2 from a gas discharge port provided at the top of the cleaning tank 39. Meanwhile, the cooling water W, the temperature of which has risen by contact with the gas at the filling material 40, flows down to the bottom part of the cleaning tank 39, passes through the cooling pipe 41, is cooled by the cooler 43, and is then supplied again from the upper part of the cleaning tank 39.

The filling material 23, the filling material 27, and the filling material 40 of the carbon dioxide capture apparatus 20 are provided to increase the contact area between the supplied gas and the liquid, in a similar manner to the filling material 12 of the pretreatment apparatus 10. The filling material 23, the filling material 27, and the filling material 40 are made from an iron-based metal material, such as stainless steel or carbon steel; however, they are not limited to this material, and a material having durability and corrosion resistance at the processing temperature and having a shape with a desired contact area can be appropriately selected and used.

The gas-liquid separation unit 45 separates moisture from the gas discharged from the separation apparatus 25. The gas-liquid separation unit 45 includes an exhaust pipe 46, a liquid feed pipe 47, a cooler 48, a gas-liquid separator 49, and a pump 50. The exhaust pipe 46 connects the gas discharge port of the separation tank 26 and an upper part of the gas-liquid separator 49 and is provided with the cooler 48. The liquid feed pipe 47 connects a bottom part of the gas-liquid separator 49 and the separation tank 26 and is provided with the pump 50.

A gas containing high-concentration carbon dioxide discharged from the gas discharge port of the separation apparatus 25 passes through the exhaust pipe 46 and is cooled by the cooler 48, and moisture and the alkaline solution A contained in the gas are condensed. The condensed water and the like are separated at the gas-liquid separator 49, supplied to the separation apparatus 25 through the liquid feed pipe 47 by the pump 50, and returned to the alkaline solution A at the bottom part of the separation tank 26.

The gas separated by the gas-liquid separation unit 45 contains, for example, carbon dioxide in a mass ratio of 90% or more and is supplied to the first generation apparatus 60 through a connection pipe 51. The gas containing high-concentration carbon dioxide and passing through the connection pipe 51 is supplied with hydrogen, the flow rate of which is adjusted by a flow rate control valve 52. The type of hydrogen is not limited, and hydrogen obtained by electrolysis of water using renewable energy, such as solar, wind, or hydropower, is usable, for example. The mixed gas containing carbon dioxide and hydrogen is compressed by a compressor 53 and supplied to the first generation apparatus 60. The ratio of the amount of hydrogen to the amount of carbon dioxide supplied to the first generation apparatus 60 can be set appropriately and may be, for example, 2 or more or 2.5 or more in molar ratio. The ratio of the amount of hydrogen to the amount of carbon dioxide supplied to the first generation apparatus 60 may be, for example, less than 4 or less than 3.5 in molar ratio.

The first generation apparatus 60 generates a hydrocarbon with two or more carbon atoms from a first raw material containing carbon dioxide and hydrogen. In the present embodiment, carbon dioxide in the first raw material includes carbon dioxide separated at the carbon dioxide capture apparatus 20. Specifically, the carbon dioxide in the first raw material includes carbon dioxide separated at the separation apparatus 25. Thus, high-concentration carbon dioxide is usable as the first raw material. This improves generation efficiency of the hydrocarbon with two or more carbon atoms. However, as long as it is possible to generate the hydrocarbon with two or more carbon atoms, it is unnecessary to use the carbon dioxide separated at the carbon dioxide capture apparatus 20 for the carbon dioxide in the first raw material.

Carbon dioxide has been regarded as a cause of global warming in recent years, and there has been a worldwide movement to curb carbon dioxide emissions. Generation of a hydrocarbon with two or more carbon atoms from carbon dioxide contained in a plant exhaust gas and the like reduces the amount of carbon dioxide to be released into the atmosphere, and a hydrocarbon with two or more carbon atoms has high utility value in the market. Moreover, if carbon dioxide is used as a raw material to generate a hydrocarbon, such as ethylene, which is a raw material for plastics, it is possible to reduce use of petroleum, a limited resource, and to reduce carbon dioxide emissions.

For the first generation apparatus 60, a known reactor is usable, for example, a shell and tube type reactor, or a flat plate type reactor. The shell and tube type reactor is inexpensive due to its simple structure. The flat plate type reactor has high heat exchange efficiency and is superior in removing heat of reaction and improving reaction efficiency. In the present embodiment, the first generation apparatus 60 includes a reactor 61, a cooling pipe 62, a pump 63, and a cooler 64. The cooling pipe 62 connects the upstream side and the downstream side of the reactor 61, and the pump 63 and the cooler 64 are connected to the cooling pipe 62.

The reactor 61 has a catalyst arranged in a flow path through which the first raw material passes, and when the first raw material comes into contact with the catalyst, a hydrocarbon with two or more carbon atoms is generated. The type of catalyst arranged in the first generation apparatus 60 is not limited as long as a hydrocarbon with two or more carbon atoms is generated from the first raw material. The catalyst is selected from the viewpoint of the type of hydrocarbon generated, and a known catalyst, such as an iron catalyst or a cobalt catalyst, is usable. An iron catalyst mainly generates a light hydrocarbon, and a cobalt catalyst mainly generates a heavy hydrocarbon including wax. An iron catalyst mainly generates an olefin and paraffin, and a cobalt catalyst mainly generates paraffin. Note that an iron catalyst is a catalyst containing iron as an active component, and a cobalt catalyst is a catalyst containing cobalt as an active component. Preferably, the content of the active component is 20% by mass or more of the whole catalyst. Preferably, the first generation apparatus 60 is provided with an iron catalyst for generating a hydrocarbon with two or more carbon atoms from the first raw material. This generates a light olefin (low-grade olefin), which is usable as a raw material for plastics. In the first generation apparatus 60, the types of reaction conditions are not limited as long as a hydrocarbon with two or more carbon atoms is generated. For example, the reaction temperature is 200 to 400° C. and the pressure is 0.1 to 2 MPa.

A product to be generated by the first generation apparatus 60 may include various compounds other than a hydrocarbon with two or more carbon atoms. A hydrocarbon with two or more carbon atoms includes, for example, an olefin and paraffin, and preferably includes a light olefin with two or more and four or less carbon atoms. An olefin with two or more and four or less carbon atoms is useful as a raw material for plastics. Examples of an olefin with two or more and four or less carbon atoms include at least one or more olefins selected from the group consisting of ethylene, propylene, 1-butene, 2-butene, isobutene, and 1,3-butadiene.

For example, ethylene is generated from carbon dioxide and hydrogen as shown in the following reaction formula (1).

$$2CO_2 + 6H_2 \rightarrow C_2H_4 + 4H_2O \qquad (1)$$

Since a standard enthalpy of the reaction at 298 K is ΔH=−128 kJ/mol and the reaction is exothermic, it is preferable to cool the reaction zone to an appropriate temperature to improve the generation efficiency of ethylene. In the present embodiment, the pump 63 circulates a known refrigerant between the reactor 61 and the cooling pipe 62 to lower the temperature of the reaction zone. At this time, at least a part of the heat of reaction when a hydrocarbon with two or more carbon atoms is generated in the first generation apparatus 60 may be recovered. It is thus possible to effectively utilize excess heat of reaction. For example, at least a part of the heat of reaction may be subjected to heat exchange with a known refrigerant for cooling the cooler 64, and the resulting thermal energy may be reused in the hydrocarbon generation system 1.

The separation apparatus 25 of the carbon dioxide capture apparatus 20 may separate carbon dioxide from the alkaline solution A containing carbon dioxide by using at least a part of the heat of reaction when a hydrocarbon with two or more carbon atoms is generated in the first generation apparatus 60. The energy required for separating carbon dioxide from the alkaline solution A by means of the separation apparatus 25 is, for example, 250 GJ/t-$CO_2$, and the heat of reaction recovered by the first generation apparatus 60 is, for example, 40.8 GJ/t-$CO_2$. Thus, exchanging the heat of the steam for heating the heater 30 of the separation apparatus 25 with the heat of the refrigerant for cooling the cooler 64 of the first generation apparatus 60 enables excess heat of reaction in the first generation apparatus 60 to be effectively utilized.

As described above, the first generation apparatus 60 generates a hydrocarbon with two or more carbon atoms, which is a valuable substance, from carbon dioxide, which causes global warming. In the first generation apparatus 60, a hydrocarbon with two or more carbon atoms is generated from, for example, 20% by mass or more and less than 85% by mass of the carbon dioxide contained in the first raw material, depending on reaction conditions. The ratio of the hydrocarbon with two or more carbon atoms generated depends on reaction conditions and may be 35% by mass or more, or may be 50% by mass or more. The ratio of the hydrocarbon with two or more carbon atoms generated may be 65% by mass or less, or 55% by mass or less.

A part of the carbon dioxide supplied to the first generation apparatus 60 is not used for generation of the hydrocarbon and is discharged from the first generation apparatus 60 as an unreacted portion. The ratio of carbon dioxide discharged from the first generation apparatus 60 out of the carbon dioxide supplied to the first generation apparatus 60 may be 15% by mass or more, or may be 45% by mass or more. The ratio of carbon dioxide discharged from the first generation apparatus 60 out of the carbon dioxide supplied to the first generation apparatus 60 may be less than 80% by mass or may be less than 50% by mass.

A product P1 containing the hydrocarbon with two or more carbon atoms, generated in the first generation apparatus 60 may be separated on a connection pipe 65 connecting a discharge port of the first generation apparatus 60 and a supply port of the second generation apparatus 70 or may be separated at a downstream side of the second generation apparatus 70. Meanwhile, a gas discharged from the first generation apparatus 60 and containing carbon dioxide is supplied to the second generation apparatus 70 through the connection pipe 65. The gas containing carbon dioxide and passing through the connection pipe 65 is supplied with hydrogen, the flow rate of which is adjusted by a flow rate control valve 66. Hydrogen obtained by utilizing renewable energy as described above may be used. The mixed gas containing carbon dioxide and hydrogen is compressed by a compressor 67 and supplied to the second generation apparatus 70. The ratio of the amount of hydrogen to the amount of carbon dioxide supplied to the second generation apparatus 70 can be set appropriately and may be, for example, 3 or more, or may be 3.5 or more in molar ratio. The ratio of the amount of hydrogen to the amount of carbon dioxide supplied to the second generation apparatus 70 may be less than 5 or may be less than 4.5.

In the present embodiment, the compressor 67 is used when the mixed gas containing hydrogen and carbon dioxide is supplied as a second raw material to the second generation apparatus 70. However, the gas discharged from the first generation apparatus 60 may be supplied to the second generation apparatus 70 with its pressure maintained. Specifically, without providing the compressor 67 between the first generation apparatus 60 and the second generation apparatus 70, a gas discharged from the discharge port of the first generation apparatus 60 may be supplied through the supply port of the second generation apparatus 70 as it is without adjusting its pressure. This enables the pressure in the reactor 71 to be maintained at a level suitable for generation of methane, and energy required in the compressor 67 to be reduced.

The second generation apparatus 70 mainly generates methane from the second raw material containing: hydrogen; and carbon dioxide contained in the first raw material and discharged from the first generation apparatus 60. That is, the first generation apparatus 60 and the second generation apparatus 70 are arranged in series, and the second generation apparatus 70 is arranged downstream of the first generation apparatus 60. The second generation apparatus 70 generates methane from carbon dioxide and hydrogen as shown in the following reaction formula (2).

$$CO_2 + 4H_2 \rightarrow CH_4 + 2H_2O \qquad (2)$$

The reaction formula (2) is called methanation (or the Sabatier reaction), and it is possible to generate methane with high selectivity. That is, a mass ratio of methane generated from carbon dioxide supplied to the second generation apparatus 70 is larger than a mass ratio of a hydrocarbon with two or more carbon atoms generated from carbon dioxide supplied to the first generation apparatus 60. The second generation apparatus 70 generates methane from, for example, 85% by mass or more of the carbon dioxide contained in the second raw material, depending on reaction conditions. The ratio of methane generated depends on reaction conditions and may be 90% by mass or more, or may be 95% by mass or more. As described above, the first generation apparatus 60 generates a hydrocarbon with two or more carbon atoms from, for example, 20% by mass or more and less than 85% by mass of the carbon dioxide contained in the first raw material. However, arranging the second generation apparatus 70 in series on the downstream side of the first generation apparatus 60 enables the unreacted carbon dioxide discharged from the first generation apparatus 60 to be effectively utilized in the second generation apparatus 70.

For example, 45% by mass of carbon dioxide supplied to the first generation apparatus 60 is consumed to generate a hydrocarbon with two or more carbon atoms, and 55% by mass of the carbon dioxide is discharged from the first generation apparatus 60 as an unreacted portion. However, 90% by mass of the carbon dioxide is consumed to generate methane by the second generation apparatus 70. That is, only 10% by mass of the carbon dioxide discharged from the first generation apparatus 60 as an unreacted portion is discharged from the second generation apparatus 70 as an unreacted portion. Therefore, across the whole of the first generation apparatus 60 and the second generation apparatus 70, 94.5% by mass of carbon dioxide input as raw materials is used for the generation of methane and a hydrocarbon other than the methane, and only about 5.5% by mass of the carbon dioxide is discharged. That is, the hydrocarbon generation system 1 is capable of generating a hydrocarbon with two or more carbon atoms and methane from 90% by mass or more of the carbon dioxide contained in the first raw material. Therefore, the hydrocarbon generation system 1 according to the present embodiment efficiently captures carbon dioxide, which is a cause of global warming, and generates methane and a hydrocarbon with two or more carbon atoms, which are valuable substances, at a high yield in the hydrocarbon generation system 1 as a whole.

It is also conceivable that carbon dioxide discharged from the first generation apparatus 60 be fed into the first generation apparatus 60 again as a raw material to improve the hydrocarbon yield across the whole system. However, in order to generate a large amount of a hydrocarbon with two or more carbon atoms from carbon dioxide in the first generation apparatus 60, it is necessary to repeat the work of supplying carbon dioxide discharged from the first generation apparatus 60 to the first generation apparatus 60 multiple times. For example, assuming that 55% by mass of the carbon dioxide supplied to the first generation apparatus 60 is discharged from the first generation apparatus 60, even if the reaction in the first generation apparatus 60 is repeated four times, only 92% by mass of the carbon dioxide reacts.

As with the first generation apparatus 60, a known reactor is usable for the second generation apparatus 70, for example, a shell and tube type reactor or a flat plate type reactor. In the present embodiment, the second generation apparatus 70 includes the reactor 71, a cooling pipe 72, a pump 73, and a cooler 74. The upstream and downstream sides of the reactor 71 are connected by the cooling pipe 72, which is provided with the pump 73 and the cooler 74.

The reactor 71 has a catalyst arranged in a flow path through which the second raw material passes, and when the second raw material comes into contact with the catalyst, methane is generated. The type of catalyst arranged in the reactor 71 is not limited as long as methane is generated from the second raw material. A known catalyst used for methanation, such as a nickel catalyst or a ruthenium catalyst, is usable. A nickel catalyst is a catalyst containing nickel as an active component, and a ruthenium catalyst is a catalyst containing ruthenium as an active component. Preferably, the content of the active component is 20% by mass or more of the whole catalyst. From the viewpoint of cost and high methane selectivity, it is preferable that the second generation apparatus 70 be provided with the nickel catalyst for generating methane from the second raw material. In the second generation apparatus 70, the types of reaction conditions are not limited as long as methane is generated. For example, the reaction temperature is 200 to 400° C. and the pressure is 0.1 to 2 MPa.

Since a standard enthalpy of the reaction of the above-described reaction formula (2) at 298 K is $\Delta H = -165$ kJ/mol and the reaction is exothermic, it is preferable to cool the reaction zone to an appropriate temperature to improve generation efficiency of methane. In the present embodiment, the pump 73 circulates a known refrigerant between the reactor 71 and the cooling pipe 72 to lower the temperature of the reaction zone. As with the first generation apparatus 60, at least a part of heat of reaction when the methane is generated in the second generation apparatus 70 may be recovered in the hydrocarbon generation system 1. This enables the excess heat of reaction to be effectively utilized. For example, at least a part of the heat of reaction may be subjected to heat exchange with a known refrigerant for cooling the cooler 74, and the resulting thermal energy may be reused in the hydrocarbon generation system 1.

The separation apparatus 25 of the carbon dioxide capture apparatus 20 may separate carbon dioxide from the alkaline solution A containing carbon dioxide by using at least a part of the heat of reaction when methane is generated in the second generation apparatus 70. The energy required for separating carbon dioxide from the alkaline solution A by means of the separation apparatus 25 is, for example, 250 GJ/t-$CO_2$, and the heat of reaction recovered by the second generation apparatus 70 is, for example, 152.6 GJ/t-$CO_2$. Thus, exchanging the heat of the steam for heating the heater 30 of the separation apparatus 25 with the heat of the refrigerant for cooling the cooler 74 of the second generation apparatus 70 enables excess heat of reaction generated in the second generation apparatus 70 to be effectively utilized.

The second generation apparatus 70 discharges a mixed gas containing a product P2 containing methane, and carbon dioxide. Then, the product P2 containing methane is separated from the mixed gas, and a gas G3 containing the carbon dioxide is discharged.

Note that in the above-described embodiment, a raw material containing carbon dioxide was used as the first raw material for the first generation apparatus 60 to generate the hydrocarbon with two or more carbon atoms. Also a raw material containing carbon dioxide was used as the second raw material for the second generation apparatus 70 to generate the hydrocarbon. However, a raw material containing carbon monoxide, instead of the carbon dioxide or in combination with the carbon dioxide, may be used as the first raw material. Similarly, a raw material containing carbon monoxide, instead of the carbon dioxide or in combination with the carbon dioxide, may be used as the second raw material. When the carbon monoxide and hydrogen are reacted in the first generation apparatus 60, depending on reaction conditions, 20% by mass or more and less than 85% by mass of the supplied carbon monoxide becomes a hydrocarbon with two or more carbon atoms, and at least one of carbon monoxide or carbon dioxide is discharged as an unreacted portion. Therefore, the second generation apparatus 70 uses a raw material containing the unreacted carbon monoxide and/or carbon dioxide as the second raw material and generates methane. When a raw material containing carbon monoxide and hydrogen is used as the second raw material for the second generation apparatus 70 to generate methane, 85% by mass or more of the supplied carbon monoxide becomes methane, as in the case of using the raw material containing carbon dioxide as the second raw material. Therefore, even when at least one of carbon monoxide or carbon dioxide is contained in the first raw material, methane is generated from the second raw material containing carbon monoxide and/or carbon dioxide discharged from the first generation apparatus 60.

When the first raw material contains carbon monoxide, the first generation apparatus 60 generates ethylene from carbon monoxide and hydrogen as shown in the following reaction formula (3).

$$2CO + 4H_2 \rightarrow C_2H_4 + 2H_2O \tag{3}$$

A standard enthalpy of the reaction at 298 K is ΔH=−210 kJ/mol, and the reaction is exothermic. Therefore, at least a part of the heat of reaction may be recovered and reused in the hydrocarbon generation system 1 as in the case of using carbon dioxide as a raw material.

Similarly, when the second raw material contains carbon monoxide, the second generation apparatus 70 generates methane from carbon monoxide and hydrogen as shown in the following reaction formula (4).

$$C_0 + 3H_2 \rightarrow CH_4 + H_2O \tag{4}$$

A standard enthalpy of the reaction at 298 K is ΔH=−206 kJ/mol, and the reaction is exothermic. Thus, at least a part of the heat of reaction may be recovered and reused in the hydrocarbon generation system 1 as in the case of using carbon dioxide as a raw material.

Therefore, at least a part of one of the heat of reaction when a hydrocarbon with two or more carbon atoms is generated in the first generation apparatus 60, or the heat of reaction when methane is generated in the second generation apparatus 70 may be recovered. The separation apparatus 25 may separate carbon dioxide from the alkaline solution A containing carbon dioxide by means of at least a part of one of: the heat of reaction when a hydrocarbon with two or more carbon atoms is generated in the first generation apparatus 60; or the heat of reaction when methane is generated in the second generation apparatus 70. This improves the energy efficiency of the whole process.

Next, effects of the hydrocarbon generation system 1 are described.

The hydrocarbon generation system 1 according to the present embodiment includes the first generation apparatus 60 that generates a hydrocarbon with two or more carbon atoms from the first raw material containing: at least one of carbon monoxide or carbon dioxide; and hydrogen. The hydrocarbon generation system 1 includes the second generation apparatus 70 that generates methane from the second raw material containing: hydrogen; and at least one of carbon monoxide or carbon dioxide contained in the first raw material and discharged from the first generation apparatus 60.

The first generation apparatus 60 according to the present embodiment generates a hydrocarbon with two or more carbon atoms from the first raw material containing: at least one of carbon monoxide or carbon dioxide; and hydrogen, and is connected to the second generation apparatus 70. The second generation apparatus 70 generates methane from the second raw material containing: hydrogen; and at least one of carbon monoxide or carbon dioxide contained in the first raw material and discharged from the first generation apparatus 60.

The second generation apparatus 70 according to the present embodiment generates methane from the second raw material containing: hydrogen; and at least one of carbon monoxide or carbon dioxide contained in the first raw material and discharged from the first generation apparatus 60. The first generation apparatus 60 generates a hydrocarbon with two or more carbon atoms from the first raw material containing: at least one of carbon monoxide or carbon dioxide; and hydrogen.

The hydrocarbon generation system 1, the first generation apparatus 60, and the second generation apparatus 70 according to the present embodiment provide the following effects. That is, unreacted carbon monoxide and carbon dioxide, which are not used to generate a hydrocarbon with two or more carbon atoms, of the carbon monoxide and carbon dioxide supplied to the first generation apparatus 60, are used as raw materials for generating methane in the second generation apparatus 70. Thus, even when the yield of the hydrocarbon with two or more carbon atoms is not sufficiently obtained in the first generation apparatus 60, methane is generated with high efficiency in the second generation apparatus 70. Therefore, the hydrocarbon generation system 1 generates not only methane but also a high value hydrocarbon other than methane.

Most of the carbon monoxide and carbon dioxide contained in the first raw material are consumed by the first generation apparatus 60 and the second generation apparatus 70, and it is thus possible to reduce the amount of carbon monoxide and carbon dioxide discharged from the hydrocarbon generation system 1.

As described above, the hydrocarbon generation system 1, the first generation apparatus 60, and the second generation apparatus 70 according to the present embodiment efficiently generate methane and a hydrocarbon other than methane from at least one of carbon monoxide or carbon dioxide.

[Hydrocarbon Generation Method]

Next, a hydrocarbon generation method according to the present embodiment is described. The hydrocarbon generation method includes a first generation step and a second generation step. The first generation step is generating a hydrocarbon with two or more carbon atoms from a first raw material containing: at least one of carbon monoxide or carbon dioxide; and hydrogen, in the first generation apparatus 60 as described above. The second generation step is generating methane from a second raw material containing: hydrogen; and at least one of carbon monoxide or carbon dioxide contained in the first raw material and discharged in the first generation step, in the second generation apparatus 70 as described above.

The hydrocarbon generation method according to the present embodiment efficiently generates methane and a hydrocarbon other than methane from at least one of carbon monoxide or carbon dioxide for the same reason as described above.

Although some embodiments have been described herein, other variations and modifications of the embodiments are possible based on the above disclosure. All of the components of the above-described embodiments and all of the features described in the claims may be individually extracted and combined as long as they do not contradict each other.

The present disclosure contributes, for example, to Goal 13 of the United Nations-led Sustainable Development Goals (SDGs): "Take urgent action to combat climate change and its impacts."

What is claimed is:

1. A hydrocarbon generation system comprising:
   a first generation apparatus configured to generate a hydrocarbon with two or more carbon atoms from a first raw material containing:
      at least one of carbon monoxide or carbon dioxide; and
      hydrogen; and
   a second generation apparatus configured to generate methane from a second raw material containing:
      hydrogen; and at least one of carbon monoxide or carbon dioxide contained in the first raw material and discharged from the first generation apparatus;

wherein the first generation apparatus is provided with an iron catalyst for generating the hydrocarbon with two or more carbon atoms from the first raw material, and the second generation apparatus is provided with a nickel catalyst for generating the methane from the second raw material.

2. The hydrocarbon generation system according to claim 1, wherein the first generation apparatus generates the hydrocarbon with two or more carbon atoms from 20% by mass or more and less than 85% by mass of the carbon dioxide contained in the first raw material.

3. The hydrocarbon generation system according to claim 1, wherein the second generation apparatus generates the methane from 85% by mass or more of the carbon dioxide contained in the second raw material.

4. The hydrocarbon generation system according to claim 1, further comprising:

a carbon dioxide capture apparatus configured to capture carbon dioxide from a gas containing carbon dioxide, wherein the carbon dioxide contained in the first raw material includes carbon dioxide separated at the carbon dioxide capture apparatus.

5. The hydrocarbon generation system according to claim 4, wherein the carbon dioxide capture apparatus comprises:

an absorption apparatus configured to form an alkaline solution containing carbon dioxide by gas-liquid contact between a gas containing carbon dioxide and an alkaline solution; and a separation apparatus configured to separate carbon dioxide from the alkaline solution containing carbon dioxide, wherein the carbon dioxide contained in the first raw material includes the carbon dioxide separated at the separation apparatus.

6. The hydrocarbon generation system according to claim 5, wherein the separation apparatus separates carbon dioxide from the alkaline solution containing carbon dioxide by using at least a part of one of heat of reaction when the hydrocarbon with two or more carbon atoms is generated in the first generation apparatus, or heat of reaction when the methane is generated in the second generation apparatus.

7. The hydrocarbon generation system according to claim 1, wherein at least a part of one of heat of reaction when the hydrocarbon with two or more carbon atoms is generated in the first generation apparatus, or heat of reaction when the methane is generated in the second generation apparatus is recovered.

8. The hydrocarbon generation system according to claim 1, wherein the hydrocarbon with two or more carbon atoms comprises an olefin with two or more and four or less carbon atoms.

9. The hydrocarbon generation system according to claim 1, wherein a gas discharged from the first generation apparatus is supplied to the second generation apparatus with the pressure of the gas being maintained.

10. A hydrocarbon generation method, comprising:

a first generation step of generating, in a first generation apparatus, a hydrocarbon with two or more carbon atoms from a first raw material containing:

at least one of carbon monoxide or carbon dioxide; and hydrogen; and a second generation step of generating, in a second generation apparatus, methane from a second raw material containing:

hydrogen; and at least one of carbon monoxide or carbon dioxide contained in the first raw material and discharged in the first generation step;

wherein the first generation apparatus is provided with an iron catalyst for generating the hydrocarbon with two or more carbon atoms from the first raw material, and the second generation apparatus is provided with a nickel catalyst for generating the methane from the second raw material.

* * * * *